United States Patent
Fukatsu et al.

(10) Patent No.: US 7,899,684 B2
(45) Date of Patent: Mar. 1, 2011

(54) MEDICAL REPORT CREATING APPARATUS, MEDICAL REPORT REFERENCING APPARATUS, MEDICAL REPORT CREATING METHOD, AND MEDICAL REPORT CREATION PROGRAM RECORDING MEDIUM

(75) Inventors: Hiroshi Fukatsu, Nagoya (JP); Kota Ishikawa, Anjo (JP); Akira Iwasa, Nasushiobara (JP); Kenichi Niwa, Otawara (JP)

(73) Assignees: National University Corporation Nagoya University, Nagoya-shi (JP); Toshiba Medical Systems Corporation, Otawara-shi (JP)

( * ) Notice: Subject to any disclaimer, the term of this patent is extended or adjusted under 35 U.S.C. 154(b) by 1327 days.

(21) Appl. No.: 11/099,475

(22) Filed: Apr. 6, 2005

(65) Prior Publication Data
US 2005/0226405 A1 Oct. 13, 2005

(30) Foreign Application Priority Data
Apr. 7, 2004 (JP) ................................. 2004-113533

(51) Int. Cl.
*G06Q 10/00* (2006.01)
(52) U.S. Cl. ............................................. 705/2; 705/3
(58) Field of Classification Search .................. 705/2, 3, 705/4
See application file for complete search history.

(56) References Cited

U.S. PATENT DOCUMENTS

| 6,272,470 | B1 | 8/2001 | Teshima | |
|---|---|---|---|---|
| 2004/0107118 | A1* | 6/2004 | Harnsberger et al. | 705/2 |
| 2005/0063575 | A1* | 3/2005 | Ma et al. | 382/128 |
| 2007/0150562 | A1* | 6/2007 | Stull et al. | 709/223 |

FOREIGN PATENT DOCUMENTS

| JP | 4-96152 | 3/1992 |
|---|---|---|
| JP | 7-13846 | 1/1995 |
| JP | 10-40062 | 2/1998 |
| JP | 10-79770 | 3/1998 |
| JP | 10-124523 | 5/1998 |
| JP | 2003-141022 | 5/2003 |
| JP | 2003-296451 | 10/2003 |
| WO | WO 01/95151 | 12/2001 |

OTHER PUBLICATIONS

U.S. Appl. No. 11/563,106, filed Nov. 24, 2006, Fukatsu, et al.
U.S. Appl. No. 12/358,637, filed Jan. 23, 2009, Minakuchi, et al.
(Continued)

*Primary Examiner* — Gerald J. O'Connor
*Assistant Examiner* — Edward Winston
(74) *Attorney, Agent, or Firm* — Oblon, Spivak, McClelland, Maier & Neustadt, L.L.P.

(57) ABSTRACT

A medical report creating apparatus in which a link corresponding range is specified for any of strings arranged in an observation column in a medical report display screen. Then, a drag operation is input which specifies any of contents being displayed on a monitor. When a dragged display icon is dropped onto a link corresponding range displayed portion of a medical report creation screen to specify the string, address information on the content is acquired. The address information on the referenced content is then pasted to the string. At the same time, the string in the link corresponding range has its color changed and is underlined for identification. After the report has been completed, a file is saved and the series of operations are finished. Then, the file is transferred to, for example, an image interpretation report requester.

18 Claims, 6 Drawing Sheets

OTHER PUBLICATIONS

U.S. Appl. No. 12/062,209, filed Apr. 3, 2008, Minakuchi, et al.
U.S. Appl. No. 11/442,333, filed May 30, 2006, Iwasa, et al.
U.S. Appl. No. 12/173,274, filed Jul. 15, 2008, Matsue, et al.
U.S. Appl. No. 12/409,945, filed Mar. 24, 2009, Niwa, et al.
U.S. Appl. No. 12/422,405, filed Apr. 13, 2009, Futami, et al.
U.S. Appl. No. 12/536,007, filed Aug. 5, 2009, Minakuchi et al.
Homepage Builder V6.5 With HotMedia, User's Guide 2, Reference Version, First Edition, IBM Japan, Nov. 2001, $1^{st}$ Edition, pp. 202, 203 and 311-328.

* cited by examiner

MEDICAL REPORT CREATING APPARATUS, MEDICAL REPORT REFERENCING APPARATUS, MEDICAL REPORT CREATING METHOD, AND MEDICAL REPORT CREATION PROGRAM RECORDING MEDIUM

CROSS-REFERENCE TO RELATED APPLICATIONS

This application is based upon and claims the benefit of priority from prior Japanese Patent Application No. 2004-113533, filed Apr. 7, 2004, the entire contents of which are incorporated herein by reference.

BACKGROUND OF THE INVENTION

1. Field of the Invention

The present invention relates to a medical report creating apparatus operating in a medical information system to create, for example, a report on results of interpretation of medical images that a medical specialist is requested to interpret, and in particular, to a technique for allowing the easy linkage of a string in observations in a report to an image, a past medical report, or another file which corresponds to the contents of the string.

2. Description of the Related Art

Acts of medical treatment have hitherto been classified into a large number of technical fields. Medical specialists have been commonly requested to interpret medical images obtained using an image diagnosis apparatus such as X ray diagnostic apparatus, X ray CT apparatus, and MRI apparatus. When requested to interpret such an image, a medical specialist causes the image to be displayed, makes a report on it (a report on interpretation of the medical image; referred to as a medical report below), and delivers the report to the requester.

An apparatus that electronically creates such a medical report has already been put to practical use. With this apparatus, for example, medical images delivered by the requester through network distribution are stored in a server. When the image interpreter gives an instruction on creation of a medical report, the apparatus displays a sheet used to create a report, on a screen, and accepts inputs to required items shown in the sheet. Then, the apparatus sequentially displays the images to be interpreted in accordance with the image interpreter's input instructions. If the image interpreter has added his or her opinion to observations on the images, the apparatus enters the opinion in an observation column in the sheet. If the image interpreter has input the results of a diagnosis on the basis of the image observations and in view of the requester's purpose of the check, the apparatus writes the contents of the results to a diagnosis column. On this occasion, for images pointed out in the observations, the apparatus can create and paste reduced/enlarged images or cut images to an image pasted column or the like as required. The apparatus then delivers sheet data in the medical report created using the above procedure, to the requester through, for example, a network.

For reports created using conventional medical report creating apparatuses such as the one described above, some people have pointed out difficulties in understanding the relationship between the contents of the entries in the observations and the pasted images. For example, if a plurality of similar images is pointed out in the sentences of the observations, the images pointed-out may be mistaken. Further, if pasted images are displayed on the report screen, the observation information may not be correctly understood depending on the resolution of a monitor or the size of the screen. Furthermore, if the image interpreter desires to reference not only images to be interpreted but also a past medical report, historical information, and the like, the image interpreter must perform a cumbersome operation of reading, editing, and pasting information files to the report.

Jpn. Pat. Appln. KOKAI Publication No. 1998-079770 provides a technique for utilizing link information required to reference a particular group of files as external information in order to share diagnostic information in an electronic health record system. However, the technique described in this publication only enables any medical institutions to extract a particular group of files on the basis of link information by presenting a patient card in which the link information is stored. Accordingly, the technique cannot simply be utilized for the creation of a medical report.

BRIEF SUMMARY OF THE INVENTION

It is an object of the present invention to provide a medical report creating apparatus, a medical report reproducing apparatus which can be easily operated to create a medical report and which can process medical images to be interpreted which are referenced in observations so that a requester can accurately and easily understand the observations, as well as a medical report creating method and its program.

According to a first aspect of the present invention, there is provided a medical report creating apparatus which creates an electronic file of an image interpretation report on one or more medical images to be interpreted, the apparatus comprising information processing means for creating the electronic file of the medical report on the basis of information input in accordance with an operator's operations, first display means for displaying a creation screen for the medical report created by the information processing means, and second display means for selectively displaying at least one of contents which are referenced when the medical report is created and which include a medical image, a past medical report, and an information file, and in that the information processing means comprises string input means for inputting strings to an observation column in the medical report, range specifying means for specifying a link corresponding range in the strings in the observation column, linking processing means for acquiring address information on the contents in response to an input of specification of the content displayed on the second display means and linking the address information to the string information in the link corresponding range, and display control means for causing the first display means to identify and display the linking set on the link corresponding range.

According to a second aspect of the present invention, there is provided a medical report reproducing apparatus comprising report display means for identifying and displaying the link corresponding range in the strings in the observation column when the medical report created by the medical report creating apparatus is displayed, address information acquiring means for reading the address information on the content in accordance with the input operation of specifying the link corresponding range, and contents display means for acquiring and displaying the content on the basis of the address information.

According to a third aspect of the present invention, there is provided a medical report creating method and its program which creates an electronic file of an image interpretation report on one or more medical images to be interpreted, the method and program being characterized by comprising a display step of causing a medical report creation screen to be displayed on the basis of the electronic file and causing selective display of at least one of contents which are referenced when the medical report is created and which include a medical image, a past medical report, and an information file, a string input step of inserting strings input by an operator's operations, into an observation column in the medical report, a range specifying step of specifying a link corresponding range in the strings in the observation column, a linking step of acquiring address information on the content in response to an input of specification of the content being displayed and linking the address information to the string information in the link corresponding range, and a display control step of identifying and displaying the linking set on the link corresponding range to be identified and displayed.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

An embodiment of the present invention will be described below with reference to the drawings.

Figure 1:
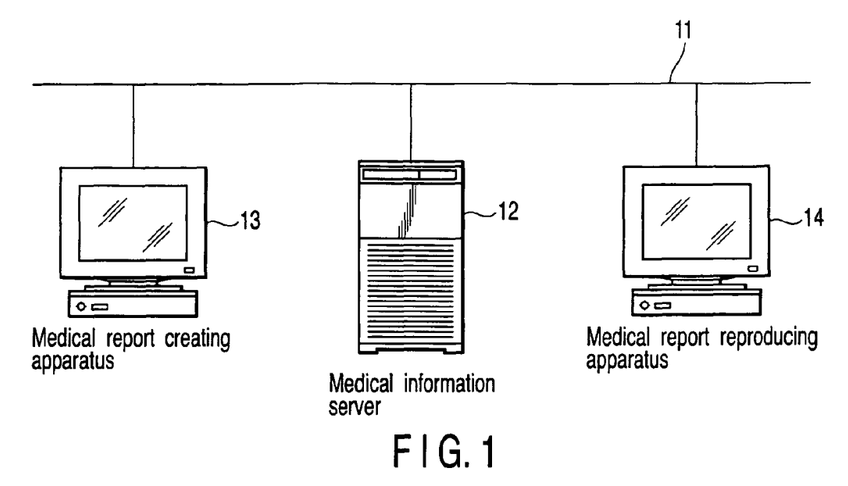
FIG. 1 is a block diagram showing the configuration of a hospital information system (HIS) including a medical report creating apparatus and a medical report reproducing apparatus according to the present invention.

FIG. 1 is a block diagram showing the configuration of a hospital information system (HIS) including a medical report creating apparatus and a medical report reproducing apparatus according to the present invention. In FIG. 1, reference numeral 11 denotes a network. The network 11 connects to a medical information server 12 that allows medical information including medical images and reports to be shared, a medical report creating apparatus 13 installed in, for example, an image interpreting room of a radiation section to create a medical report on an image requested to be interpreted, and a medical report reproducing apparatus 14 installed in each consultation room for internal medicine, surgery, or the like and which can receive and appropriately reproduce the medical report. The apparatuses 12 to 14 can communicate with one another through the network.

Although not shown in detail, the medical information server 12 according to the present embodiment includes an HIS server, an image file server, and a report system server. The medical report reproducing apparatus 14 may be a medical report exclusive apparatus but may also be, for example, a terminal of an electronic health record system installed in each consultation room.

Figure 2:
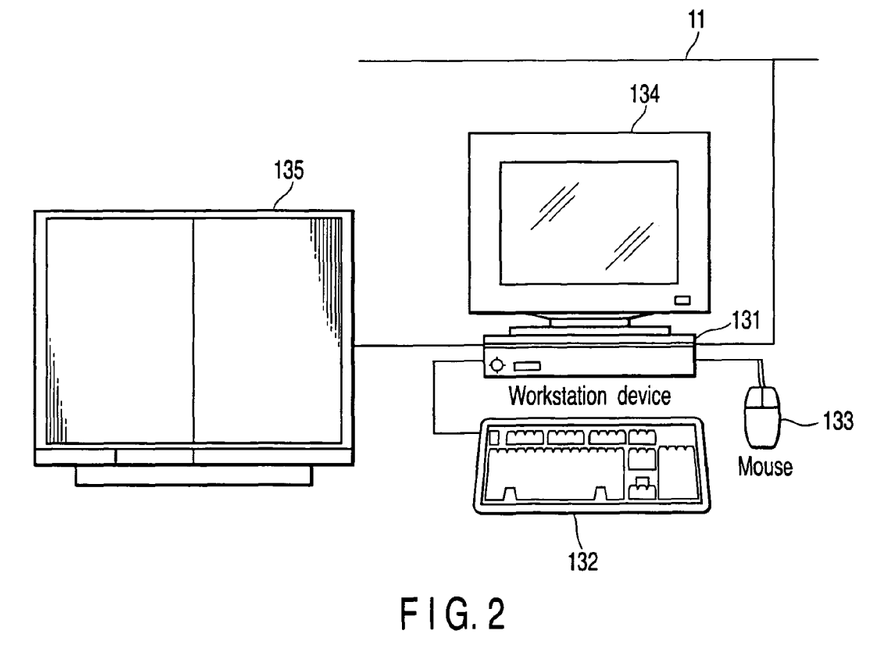
FIG. 2 is a block diagram showing the basic configuration of the medical report creating apparatus and medical report reproducing apparatus according to the present invention.

As shown in FIG. 2, the medical report creating apparatus 13 comprises a workstation device 131 connected to the network 11. The workstation device 131 connects to a keyboard 132 and a mouse 133 serving as input devices and a report monitor device 134 and a reference information monitor device 135 serving as display devices. The reference information monitor device 135 is desirably a multi-display so that many pieces of information can be monitored at a time.

Figure 3:
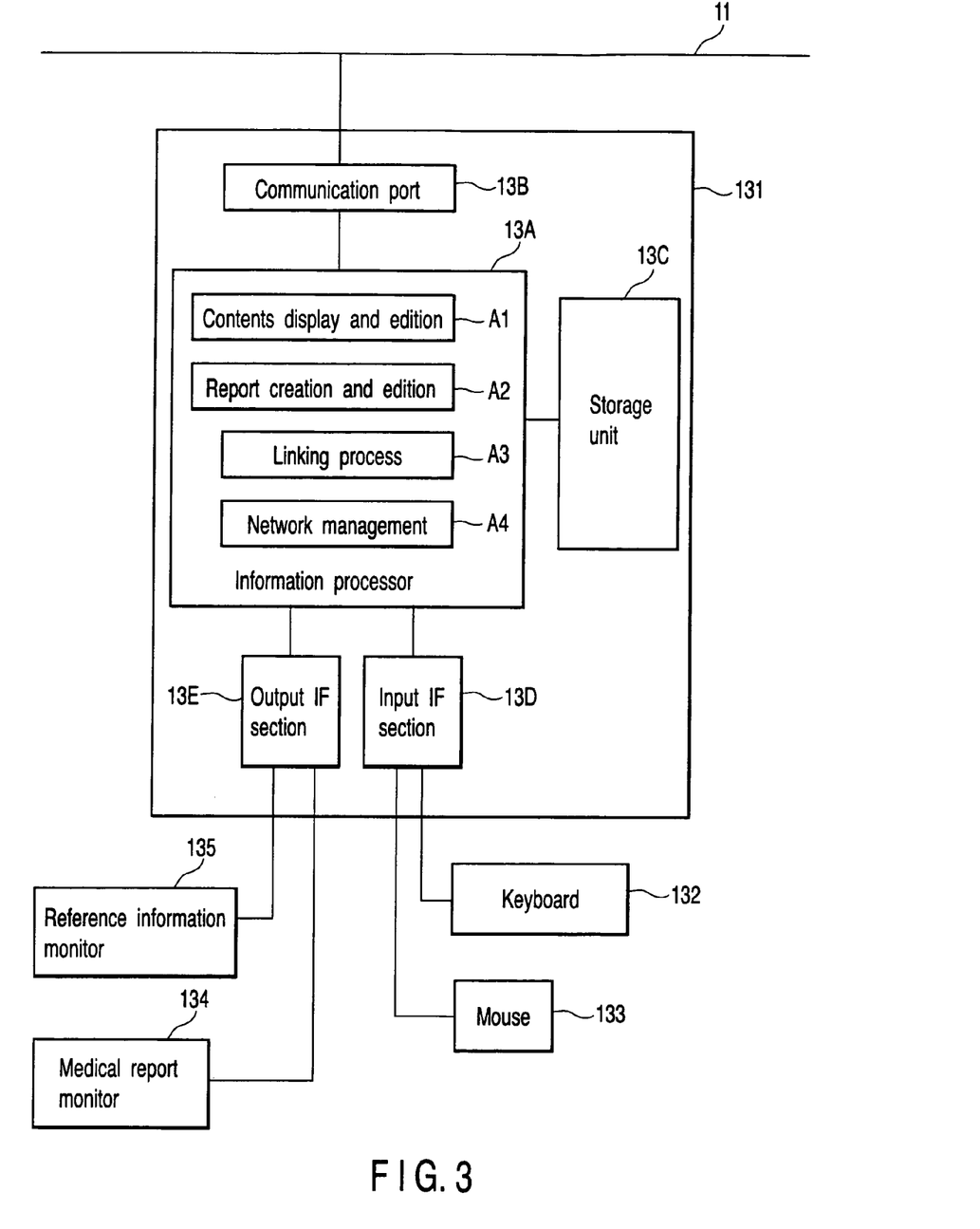
FIG. 3 is a block diagram showing an embodiment of the medical report creating apparatus according to the present invention.

As shown in FIG. 3, the workstation device 131 comprises an information processor 13A, a communication port 13B, a storage unit 13C that stores information for working, an input interface section 13D that receives instruction information corresponding to input operations performed by the keyboard 132 and mouse 133, and an output interface section 13E that outputs monitor display information to each of the report monitor device 134 and the reference information monitor device 135. A cache memory is used as the storage unit 13C. However, a hard disk device may also be used as the storage unit 13C.

The information processor 13A reads contents such as an image, a past medical report, and historical information from the medical information server 12 through the communication port 13B; the contents are to be referenced in order to create observations. The information processor 13A then stores the contents in the storage unit 13C. The information processor 13A also comprises as applications a contents display and edition program A1 that monitors various contents to carry out editions such as enlargement, reduction, and cutting, a report file creation and edition program A2 used to create and edit an electronic file of a medical report, a linking processing program A3, and a network management program A4. The information processor 13A thus selects and executes one of the programs in accordance with power-on and an operator's instruction input.

With reference to the flowchart shown in FIG. 4, description will be given of a report creating procedure executed by the medical report creating apparatus 13 configured as described above.

Figure 4:
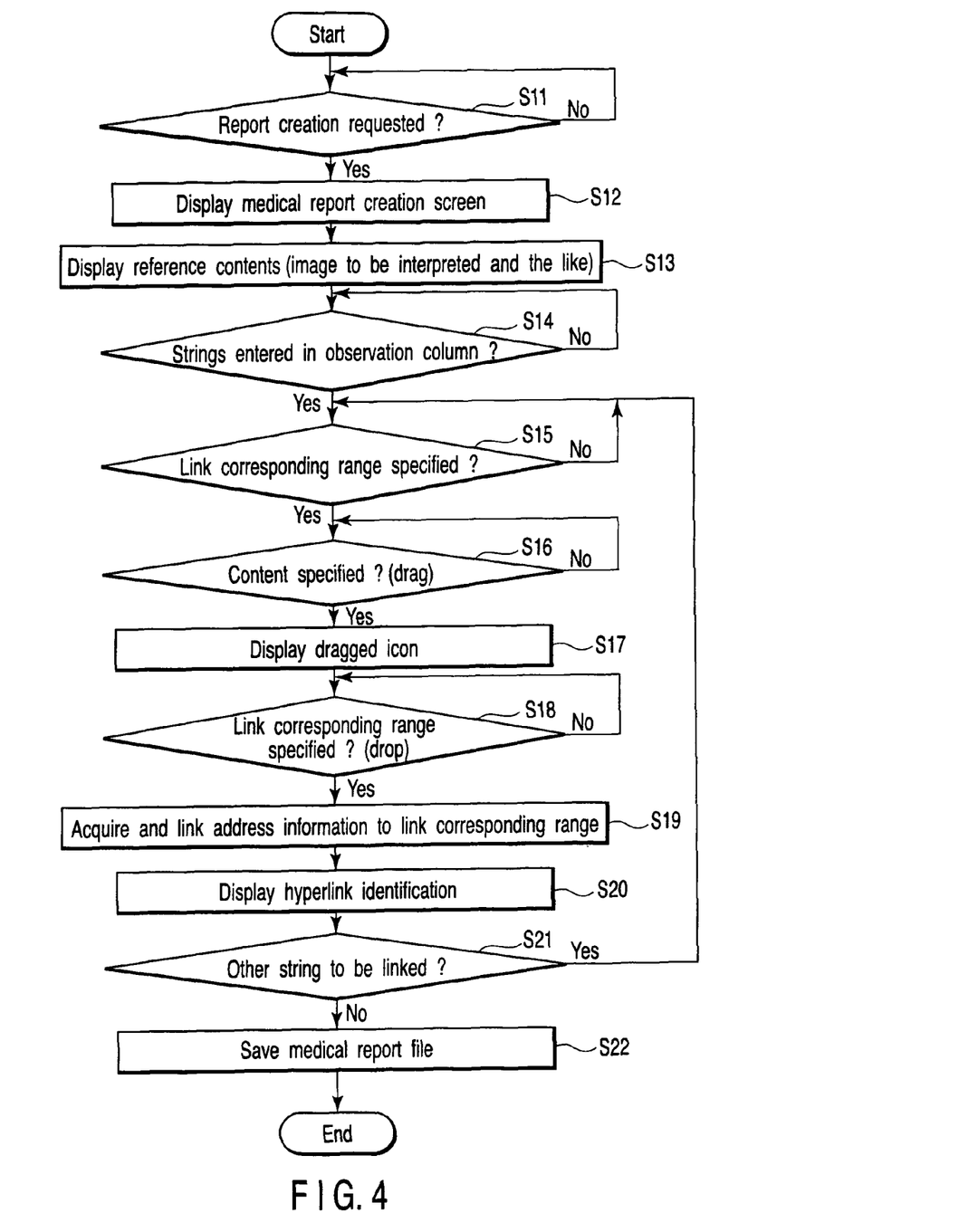
FIG. 4 is a flowchart showing a report creating procedure executed by the medical report creating apparatus shown in FIG. 3.

In FIG. 4, first, the medical report creating apparatus 13 receives a request for creation of an image interpretation report on a medical image through the network 11 (step S11). The medical report creating apparatus 13 then displays a medical report creation screen on the report monitor device 134 (step S12). The medical report creating apparatus 13 further displays an image requested to be interpreted on the reference information monitor device 135 (step S13). Here, bibliographical matters to be entered in the medical report are basically input by the operator (report creator) by operating the keyboard. However, matters described in a requested file may be automatically copied or registered information may be selected and specified. Further, besides images requested to be interpreted, the reference information monitor device 135 appropriately reads, from the medical information server 12, contents to be referenced in observations, for example, a past medical report, a diagnosis image, and historical information for display.

A medical report displayed on the monitor has an observation column. When the operator performs an operation of entering observations on the image to be interpreted, in the observation column, strings input to the observation column are appropriately arranged (step S14).

With the strings thus arranged, if contents such as an image, a past medical report, and historical information which are displayed on the reference information monitor device 135 are to be linked to a particular string, the following procedure is executed on the basis of the operator's operations.

First, the medical report creating apparatus 13 accepts an operation of placing a cursor on the string to be linked to specify a link corresponding range (step S15). Then, the medical report creating apparatus 13 accepts an operation of dragging one of the contents displayed on the monitor (step S16). At this time, the medical report creating apparatus 13 displays a drag display icon (step S17). The medical report creating apparatus 13 senses that the content has been dropped onto a display portion indicating a link corresponding range on the medical report creation screen (step S18). When the string is specified, the medical report creating apparatus 13 acquires address information on the content from the medical information server 12. The medical report creating apparatus 13 then pastes the address information on the content to be referenced, to the string in hyperlink form (step S19). At the same time, the medical report creating apparatus 13 changes the color of the string in the link corresponding range for which the hyperlink is set and underlines the string for identification (step S20).

The address information on the content is expressed as shown below.
http://[host name or IP address of server]/DLink/ins.php?ins=1.2.3&ser=4.5.6&stu=7.8.9&Mod=MR&StuDat=yyyymmdd&PatID=abcde&param=xxxxxxxxxx Here, ins: SOP instance UID,
ser: series instance UID,
stu: study instance UID,
Mod: modality,
StuDat: date on which checks were conducted,
PatID: patient ID, and
param: process parameter for image (WW/WL, enlargement rate, cut position, or annotation information).

Subsequently, the medical report creating apparatus 13 determines whether or not there is any other string to which the referenced content is to be linked (step S21). If there is another string to be linked, the medical report creating apparatus 13 returns to the operation in step S15. If there is no other string to be linked, the medical report creating apparatus 13 considers that the input of strings for observations has been finished, to save the medical report file (step S22). The medical report creating apparatus 13 thus completes the series of operations.

Figure 5:
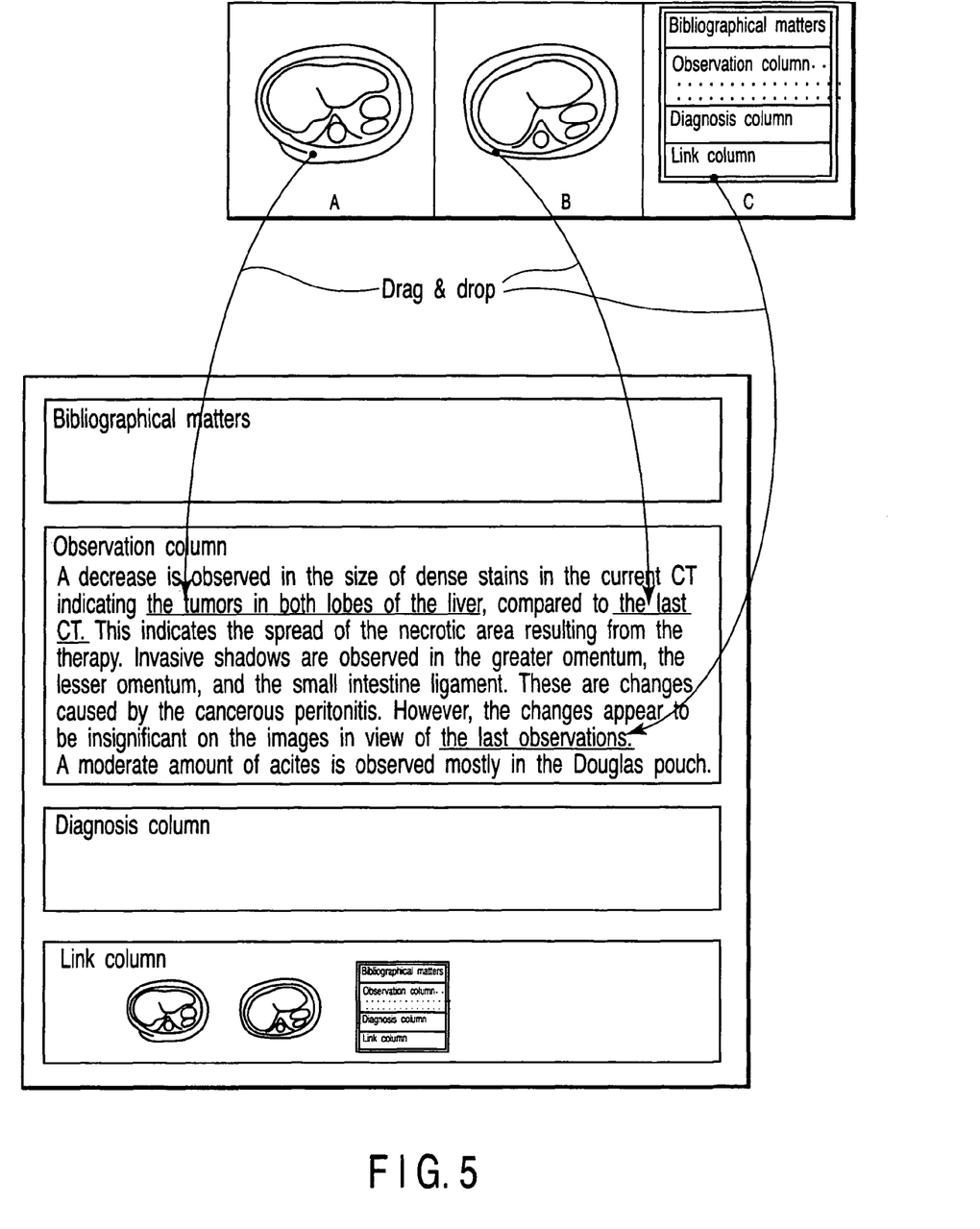
FIG. 5 is a diagram showing how a pasting process is executed using the medical report creating apparatus when a hyperlink is formed by a drag and drop operation.

FIG. 5 is a diagram showing how a hyperlink is pasted by a drag and drop operation. FIG. 5 shows the medical report creation screen and reference images A to C also displayed on the monitor. The display screen illustrated in FIG. 5 shows a column in which bibliographical matters such as a patient's name, age, and clinical history, the purpose of the check, and scan conditions are entered (an observation column), a column in which the results of a diagnosis are entered (a diagnosis column), and a list of contents linked to the observation column (link list). The example of monitor display shows three reference images A, B, and C.

In this example, description will be given to the case where the reference image A is linked to one of the strings in the observation column, the string "tumors in both lobes of the liver". The operator first specifies the string "tumors in both lobes of the liver" as a link corresponding range. The operator then drags and drops the reference image A onto the string "tumors in both lobes of the liver". This operation changes the color of the string "tumors in both lobes of the liver" and underlines the string for identification, thus indicating that a hyperlink is pasted to the string. On this occasion, address information on the reference image is acquired by the operation of dropping the reference image A onto the string "tumors in both lobes of the liver". The hyperlink for the address information is pasted to the corresponding string.

Description has been given of the capability of performing an easy drag & drop operation to execute linking on an arbitrary string to display a referenced content. In some cases, an incorrect content has been linked to a string and the correct content is to be linked to the string. Then, for a linking process, when an operation is performed which links address information on a content to an already linked link corresponding range, the existing link is canceled and the new address information is linked to the range. This technique enables the operator to carry out re-pasting to establish the correct link without the need to cancel the incorrect link. This makes it possible to improve operability.

Further, a plurality of contents may be linked to one string. Thus, for a linking process, when an operation is performed which links address information on contents to an already linked link corresponding range, link destination information is added. Alternatively, in view of the re-pasting of the link, the operator is allowed to choose either a mode in which the existing link is cancelled or a mode in which the link destination is added. This also makes it possible to improve operability. Alternatively, when a plurality of contents are simultaneously chosen and specified for linkage to one of the link corresponding ranges, all the selected contents may be linked to the range.

Further, depending on the contents of the observations, a reference image may be subjected to edition such as enlargement, reduction, marking, or cutting before the edited image is linked to the range. Such a process conventionally requires a cumbersome procedure of saving an edited image before linking it to the range. Thus, parameter information is automatically saved which is required to reproduce edition when the reference image is edited. Then, when address information is linked, the parameter information is added to the address information. By thus adding parameter information and using the same viewer software on a reproduction side, it is possible, when the reference image is displayed using the address information, to automatically edit the displayed image on the basis of the parameter information to reproduce an image conforming to the contents of the observations.

For example, if enlargement rate, WL (window level), WW (window width), X, and Y (monitor display position) are sequentially selected as parameter information added to address information, (0.5, 200, 300, 300, 400) is placed after a URL in the address information. This causes the image specified by the URL to be reduced to half so that the resulting image has a size of 200×300 and to be displayed at a coordinate position (300, 400).

If a large number of reference contents are linked to the observation column, then by making such arrangements as allow the linked contents to be understood at a glance, the contents may be more easily understood when the observations are viewed. Thus, as shown in the display example in FIG. 5, a region for a link list is provided in the medical report. When a reference content has been linked to a string (a drag and drop operation has been completed), a reduced version of the reference image is created and pasted to the link list. This process is executed for each link. Then, the reference contents can be displayed in the list as thumbnail images. In this case, it is more effective to link each reduced image pasted to the link list to the corresponding string and original content so that when the reduced image is specified, the destination strings is identified and displayed, with the corresponding content displayed on the monitor.

The link list may be created so that if a plurality of contents are linked to one string, either an order of date mode or an order of specification mode can be chosen as the order in which the reduced images are arranged. For example, if there is a plurality of images showing changes in the diseased part in a time-series manner, such as the current and last images, the viewer can more easily understand the observations when the images are shown in order of date rather than in order of specification. On the other hand, if the operator is to be conscious of the order of linking, the order of specification may be chosen.

In the above description, all the reduced images are pasted to and displayed in the link list for each linking. However, if the display screen is small, the area of the link list may be reduced so that when the cursor is placed on the link corresponding range in the strings, the corresponding reduced image is displayed. Various other methods may be used to display linked images.

Further, in the above embodiment, a link corresponding range is first specified. However, a content to be linked may be specified first (drag). Then, when an arbitrary string is specified as a link destination (drop), the word range of the string at the specified position may be detected and determined to be a link corresponding range. The range may then be manually adjusted as required. By providing the required modes so that the operator can choose any of them, it is possible to conveniently use the appropriate mode for the contents of checks, the number of reference contents, or the like.

Figure 6:
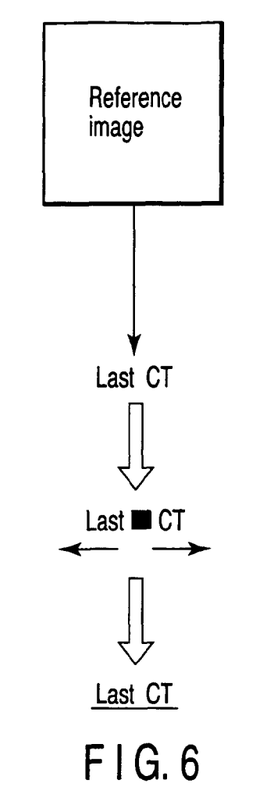
FIG. 6 is a diagram showing a process of setting a linking range when a hyperlink is formed by the drag and drop operation.

FIG. 6 shows a specific example. In this example, if a dragged image (icon) is inserted directly between strings, the area of the inserted image is laterally increased when placed on the characters. Then, the color of the characters or the number of characters specified can be changed within this range.

Figure 7:
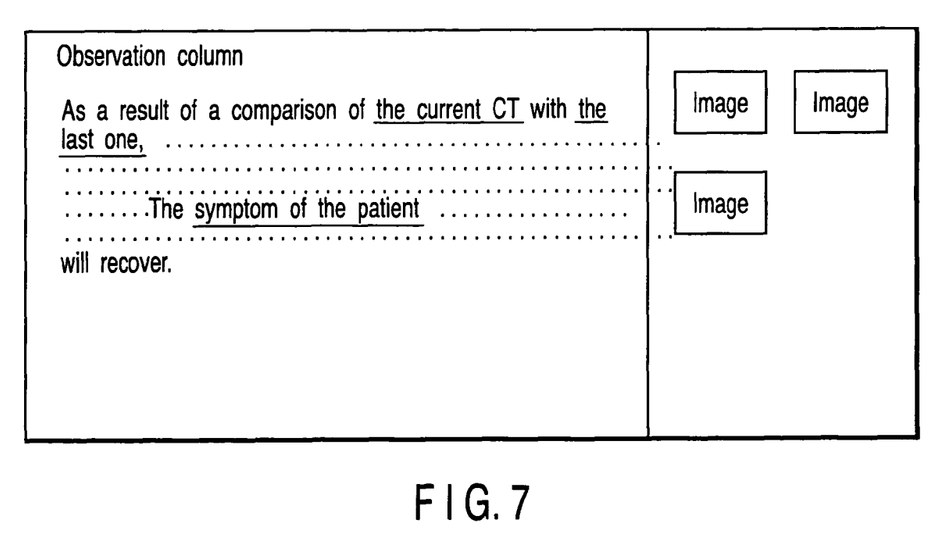
FIG. 7 is a diagram showing an example of a display provided when observations are entered using the medical report creating apparatus.

Only the characters on a report being created may be displayed in the image data (of course, characters may appear after a plurality of images have been specified) or an image may have been pasted to the characters. In this case, as shown in FIG. 7, the images are arranged in a display space next to the characters in regular order (for example, if an image has already been pasted to any characters, when a different image is further pasted to the characters, the plurality of images are pasted to the characters or the different image is additionally placed in the display area next to the characters). This display makes it possible to immediately check whether or not the link is correct. Alternatively, when an image overlapped on a string, a character or image data may be provided which indicates that the image is actually present on the string. Alternatively, if the string including the character or image data is selected, the string may be displayed in a linked form. Further, by enabling the specified character or image data to be erased which indicates that the image is actually present on the string, it is possible to easily correct the link. This enables the improvement of work efficiency.

Figure 8:
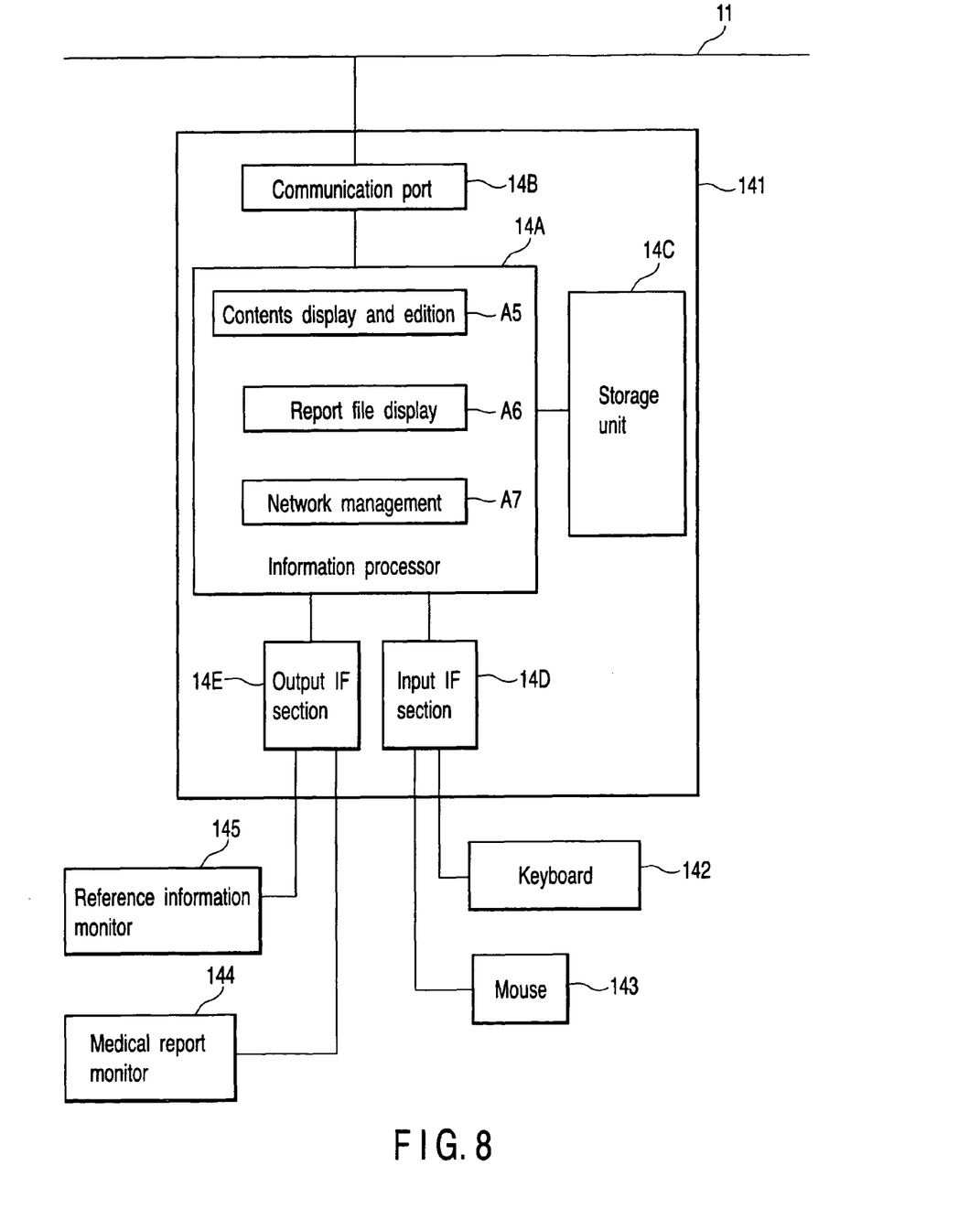
FIG. 8 is a block diagram showing an embodiment of a medical report reproducing apparatus according to the present invention.

As shown in FIG. 8, a medical report reproducing apparatus 14 has basically the same configuration of the creating apparatus shown in FIGS. 2 and 3. The medical report reproducing apparatus 14 has a workstation device 141 connected to the network 11. The workstation device 141 connects to a keyboard 142 and a mouse 143 serving as input devices and a report monitor device 144 and a reference information monitor device 145 serving as display devices. The reference information monitor device 145 is desirably a multi-display so that many pieces of reference information can be monitored. However, the reference information monitor device 145 may be composed of a single display by using a screen display such as a multi-window.

In the description below, an apparatus exclusively used to reference reports will be assumed. However, it is possible to utilize a terminal of an electronic medical report system or its reproducing apparatus.

The workstation device 141 comprises an information processor 14A, a communication port 14B, a storage unit 14C that stores information for workings, an input interface 14D that receives instruction information corresponding to input operations performed by the keyboard 142 and mouse 143, and an output interface section 14E that outputs monitor display information to the report monitor device 144 and reference information monitor device 145.

The information processor 14A reads a medical report file and reference contents linked to an observation column from the medical report creating apparatus 13 directly or via the medical information server 12. The information processor 14A then stores the reference contents in the storage unit 14C. The information processor 14A also comprises as applications a contents display and edition program A5 that monitors the reference contents to carry out editions such as enlargement, reduction, and cutting, the contents display and edition program A5 being the same as that of the creating apparatus, a report file display program A6 that displays an electronic file of a medical report, and a network management program A7. The information processor 14A thus selects and executes one of the programs in accordance with power-on and an operator's instruction input.

With the medical report reproducing apparatus 14 configured as described above, when a medical report created by the creating apparatus 13 is displayed on the monitor 144, strings to which hyperlinks in the observation column are pasted are identified and displayed. Then, when one of the strings is specified, linked address information is acquired. The content at that address is then read and displayed on the monitor 145. In this case, by enabling a link list to be selectively displayed, it is possible to effectively utilize the display space. Further, if links are pasted to reduced images in the link image, specifying any of the reduced images enables the corresponding content to be displayed on the monitor 145.

Furthermore, if edition parameter information is added to the linked address information, the parameter information is used to edit read contents for display. For example, if a reference content is subjected, during creation, to edition such as enlargement, reduction, marking, or cutting, this can be reproduced during viewing. Thus, the viewer can easily understand the intentions of the person who made the observations.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A medical report creating apparatus which creates an electronic file of a medical report on one or more medical images to be interpreted, the apparatus comprising:
information processing means for creating an observation column and a link information column in the medical report and for inserting information in the observation column and the link information column on the basis of information input in accordance with an operation of an operator, to create the electronic file;
first means for displaying a creation screen for the medical report created by the information processing means; and
second means for displaying reference contents, which are referenced when the medical report is created and which include at least one of a medical image, a past medical report, and an information file,
wherein the information processing means includes
observation column creating means for writing strings to the observation column in the medical report in accordance with the operation of the operator;
range specifying means for specifying a link corresponding range in the strings in the observation column in accordance with the operation of the operator;
linking processing means for acquiring address information on the reference contents in response to an input of specification of linking of the operator to the reference contents and linking the address information to the string information in the link corresponding range specified by the operator;
display control means for causing the first means to identify and display the linking set on the link corresponding range; and
means for creating thumbnail images indicative of the reference contents and pasting the thumbnail images in the link information column when the reference contents are linked by the link processing means.

2. The medical report creating apparatus according to claim 1, wherein the linking processing means recognizes reference contents to be linked by a drag operation which is performed for any of the reference contents displayed by the second means and recognizes a link destination by a drop operation which is performed for the link corresponding range displayed by the first means, to link the address information on the reference contents to the string information in the link corresponding range.

3. The medical report creating apparatus according to claim 2, wherein when an icon of the dragged content is placed on an arbitrary character of the observation column by a drop operation, the range specifying means automatically sets a string in a predetermined range including the character, as a link corresponding range.

4. The medical report creating apparatus according to claim 3, wherein the range specifying means comprises means for adjusting the automatically set range of the link corresponding range in accordance with the operation of the operator.

5. The medical report creating apparatus according to claim 1, wherein when an operation is performed which links the address information on the reference contents to the link corresponding range, the link processing means determines whether address information has already been linked to the link corresponding range, the link processing means linking new address information when no address information is linked, and canceling linking of old information and linking new address information when the old information has been linked.

6. The medical report creating apparatus according to claim 1, wherein when an operation is performed which links the address information on the reference contents to the link corresponding range, the link processing means determines whether address information has already been linked to the link corresponding range, the link processing means linking new address information when no address information is linked, and adding a link of new address information to a link of old information.

7. The medical report creating apparatus according to claim 1, wherein when an operation is performed which links the address information on the reference contents to the link corresponding range, the linking processing means determines whether address information has already been linked to the link corresponding range, the link processing means linking new address information when no address information is linked, and choosing one of a first mode in which a link of old address information is canceled and a second mode in which a link of new address information is added in accordance with the operator's operation.

8. The medical report creating apparatus according to claim 1, further comprising:
display editing means for editing display of the reference contents and generating parameter information required to reproduce the editing process,
wherein when the content edited by the display editing means is specified as the linked content, the linking processing means links the parameter information to the link corresponding range in addition to the address information.

9. The medical report creating apparatus according to claim 1, wherein when a plurality of reference contents are simultaneously chosen and specified so as to link to one of the link corresponding ranges, the linking processing means links all the selected reference contents to the specified link corresponding range.

10. The medical report creating apparatus according to claim 1, wherein if the plurality of reference contents are linked to the link corresponding range, the linking processing means chooses one of a first mode in which the display of the link information column is carried out in order of a date on which each reference content is created and a second mode in which the display is carried out in order of link specification in accordance with the operation of the operator.

11. The medical report creating apparatus according to claim 1, wherein the range specifying means comprises means for specifying the range in accordance with the operation of the operator in advance before a linking operation is performed.

12. The medical report creating apparatus according to claim 1, wherein the linking processing means carries out a display in the link information column in order of link specification when a plurality of reference contents are linked.

13. The medical report creating apparatus according to claim 1, wherein the linking processing means carries out a display in the link information column in order of content creation date when a plurality of reference contents are linked.

14. The medical report creating apparatus according to claim 1, wherein the information processing means further comprises:
means for reading a corresponding reference content in response to an input of specification of the thumbnail image linked to the link information column, and for displaying the reference content on the second means.

15. The medical report creating apparatus according to claim 1, wherein the information processing means further comprises:
means for identifying and displaying a string of a link destination in the observation column in accordance with an operation of specification of the thumbnail image pasted in the link information column.

16. The medical report creating apparatus according to claim 1, wherein the information processing means further comprises:
means for identifying and displaying a thumbnail image of the thumbnail images corresponding to a linked reference content when a cursor is put in the link corresponding range in the strings.

17. A medical report creating method implemented by a computer programmed as a medical report creating apparatus which creates an electronic file of a medical report on one or more medical images to be interpreted, based on information input in accordance with an operation of an operator, the method comprising:
displaying, by the medical report creating apparatus, a creation screen of an observation column and a link information column formed in the medical report on the basis of the electronic file;
displaying at least one of reference contents, which are referenced when the medical report is created and which include a medical image, a past medical report, and an information file;
writing strings input by an operation of an operator to the observation column;
specifying a link corresponding range in the strings in the observation column in accordance with the operation of the operator;
acquiring address information on the reference contents in response to an input of specification of linking of the operator to the reference contents being displayed, and linking the address information to the string information in the link corresponding range specified by the operator;
identifying and displaying the linking set on the link corresponding range; and
creating thumbnail images indicative of the reference contents and pasting the thumbnail images to the link information column when the reference contents are linked by the operator.

18. A non-transitory computer-readable medium on which a medical report creating program is recorded, the program causing a computer to create an electronic file of a medical report on one or more medical images to be interpreted, the program comprising:
information instructions for forming an observation column and a link information column in the medical report and inserting information into the observation column and the link information column based on information input in accordance with an operation of an operator to create the electronic file;
first display instructions for displaying a medical report creation screen on the basis of the electronic file; and
second display instructions for displaying at least one of reference contents, which are referenced when the medical report is created and which include a medical image, a past medical report, and an information file,
the information instructions including
observation column creating instructions for writing strings in the observation column in the medical report in accordance with the operation of the operator;
range specifying instructions for specifying a link corresponding range in the strings in the observation column in accordance with the operation of the operator;
linking instructions for acquiring address information on the reference contents in response to an input of specification of linking of the operator to the reference contents and linking the address information to the string information in the link corresponding range specified by the operator;
display control instructions for causing the first display process to identify and display the linking set on the link corresponding range; and
link information column creating instructions for creating thumbnail images indicative of the reference contents and linking the thumbnail images to the link information column when the reference contents are linked by the operator.

* * * * *